United States Patent [19]

Keil et al.

[11] Patent Number: 4,668,275

[45] Date of Patent: May 26, 1987

[54] CYCLOHEXANE-1,3-DIONE DERIVATIVES AND THEIR USE FOR CONTROLLING UNDESIRABLE PLANT GROWTH

[75] Inventors: Michael Keil, Freinsheim; Rainer Becker, Bad Durkheim; Norbert Goetz, Worms; Dieter Jahn, Edingen-Neckarhausen; Wolfgang Spiegler, Worms; Bruno Wuerzer, Otterstadt, all of Fed. Rep. of Germany

[73] Assignee: BASF Aktiengesellschaft, Fed. Rep. of Germany

[21] Appl. No.: 543,236

[22] Filed: Oct. 18, 1983

[30] Foreign Application Priority Data

Oct. 22, 1982 [DE] Fed. Rep. of Germany ....... 3239071

[51] Int. Cl.[4] .................... A01N 43/00; C07D 311/00
[52] U.S. Cl. .......................................... 71/88; 549/396
[58] Field of Search ............................ 549/396; 71/88

[56] References Cited

U.S. PATENT DOCUMENTS

| | | | |
|---|---|---|---|
| 3,950,420 | 4/1976 | Sawaki et al. | 71/88 |
| 3,989,737 | 11/1976 | Sawaki et al. | 71/88 |
| 4,350,705 | 9/1982 | Hamano et al. | 424/278 |
| 4,422,864 | 12/1983 | Becker et al. | 71/88 |

OTHER PUBLICATIONS

Chem. Abstr. vol. 90, 203557t.

*Primary Examiner*—Nicky Chan
*Attorney, Agent, or Firm*—Keil & Weinkauf

[57] ABSTRACT

Cyclohexane-1,3-dione derivatives of the formula

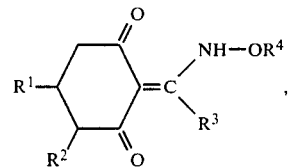

where $R^1$, $R^2$, $R^3$ and $R^4$ have the meanings stated in the description, are used for controlling undesirable plant growth.

6 Claims, No Drawings

CYCLOHEXANE-1,3-DIONE DERIVATIVES AND THEIR USE FOR CONTROLLING UNDESIRABLE PLANT GROWTH

The present invention relates to cyclohexane-1,3-dione derivatives, herbicides which contain these compounds as active ingredients and a method of controlling undesirable plant growth with these compounds.

It has been disclosed that cyclohexane-1,3-dione derivatives can be used for selectively controlling undesirable grasses in broad-leaved crops (German Laid-Open Application DOS 2,439,104).

We have found that cyclohexane-1,3-dione derivatives of the formula

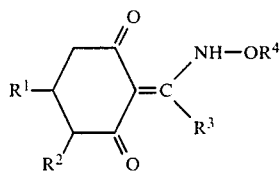

where $R^1$ is a fused ring system which consists of two aromatic or non-aromatic rings, each having 5, 6 or 7 ring members, can contain not more than three heteroatoms selected from the group consisting of oxygen, sulfur and nitrogen, and can be unsubstituted or substituted by alkyl, alkoxy, alkylthio or halogen, with the proviso that one or both of the rings contain a heteroatom if both rings are non-aromatic, $R^2$ is hydrogen, methoxycarbonyl, ethoxycarbonyl, methyl or cyano, $R^3$ is $C_1$–$C_4$-alkyl and $R^4$ is $C_1$–$C_3$-alkyl, $C_3$–$C_4$-alkenyl, $C_3$–$C_4$-haloalkenyl containing 1 to 3 halogen substituents, or propargyl, and salts of these compounds possess herbicidal activity against grasses and are tolerated by both broadleaved crops and monocotyledonous crops which do not belong to the family of the grasses (gramineae). Surprisingly, compounds of the formula I cause little or no damage to cereals.

The compounds of the formula I can occur in several isomeric and tautomeric forms, all of which are embraced by the claim:

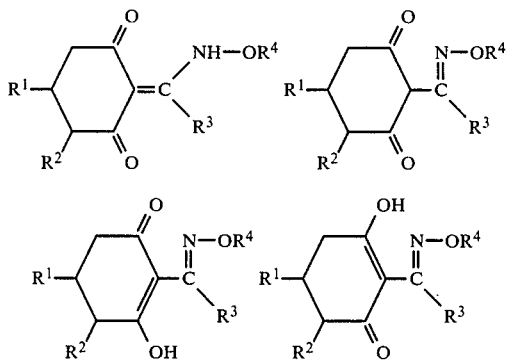

In formula I, $R^1$ is a fused ring system which consists of two rings, each having 5, 6 or 7 ring members, and can contain not more than three heteroatoms selected from the group consisting of oxygen, sulfur and nitrogen. Such a ring system can contain both aromatic and non-aromatic rings, with the proviso that one or both of the rings contain a heteroatom if both rings are non-aromatic. $R^1$ is, for example, a benzo-fused or hetaryl-fused, saturated or unsaturated 5-membered or 6-membered heterocyclic ring, such as benzofuryl, benzothienyl, indolyl, benzothiazolyl, quinolyl, quinoxalinyl, chromanyl, 2H-chromenyl, benzo-1,3-dioxolyl, benzo-1,4-dioxenyl, 2,3-dihydrobenzo[b]furyl, 1,3-dihydrobenzo[c]furyl or imidazo[1,2-a]pyridyl, eg. benzo[b]-fur-2-yl, benzo[b]fur-3-yl, benzo[b]thien-2-yl, benzo[b]-thien-3-yl, indol-3-yl, benzothiazol-2-yl, quinol-3-yl, quinol-4-yl, quinol-8-yl, quinoxalin-2-yl, chroman-3-yl, 2H-chromen-3-yl, benzo-1,3-dioxol-5-yl, benzo-1,4-dioxen-6-yl, 2,3-dihydrobenzo[b]fur-5-yl or imidazo[1,2-a]pyrid-3-yl, or is an unsaturated or partially saturated fused aromatic hydrocarbon radical consisting of two 5-membered, 6-membered or 7-membered rings, such as naphthyl, eg. naphth-1-yl or naphth-2-yl, azulenyl, eg. azulen-1-yl, tetrahydronaphthyl, eg. 1,2,3,4-tetrahydronaphth-1-yl or 1,2,3,4-tetrahydronaphth-2-yl, or indanyl, eg. indan-1-yl, or a non-aromatic fused ring system which consists of two 5-membered or 6-membered rings and contains one or more heteroatoms, such as octahydrobenzo[b]-furyl, hexahydrobenzo-1,3-dioxolyl, 4a,7,8,8a-tetrahydro-2H,5H-pyrano[4,3-b]pyranyl, 3,4,4a,7,8,8a-hexahydro-2H,5H-pyrano[4,3-b[pyranyl, hexahydrochromanyl, 4a,7,8,8a-tetrahydro-2H,5H-thiino[3,2-c]pyranyl, 3,4,4a,7,8,8a-hexahydro-2H,5H-thiino[3,2-c]pyranyl, 3a,7,8,8a-tetrahydro-2H,5H-thiino[4,3-b]pyranyl, or 3,4,4a,7,8,8a-hexahydro-2H,5H-thiino[4,3-b]pyranyl, eg. octahydro-4-benzo[b]furyl, hexahydrobenzo-1,3-dioxol-5-yl, 4a,7,8,8a-tetrahydro-2H,5H-pyrano[4,3-b]pyran-3-yl, 3,4,4a,7,8,8a-hexahydro-2H,5H-pyrano[4,3-b]-pyran-3-yl, hexahydrochroman-3-yl, 4a,7,8,8a-tetrahydro-2H,5H-thiino[3,2-c]pyran-3-yl, 3,4,4a,7,8,8a-hexahydro-2H,5H-thiino[3,2-c]pyran-3-yl, 4a,7,8,8a-tetrahydro-2H,5H-thiino[4,3-b]pyran-3-yl and 3,4,4a,7,8,8a-hexahydro-2H,5H-thiino[4,3-b]pyran-3-yl.

These radicals can be substituted by $C_1$–$C_3$-alkyl, $C_1$–$C_3$-alkoxy, $C_1$–$C_3$-alkylthio or halogen. Examples of such substituted radicals $R^1$ are 3-methylbenzo[b]fur-2-yl, 2-ethylbenzo[b]fur-3-yl, 3-chlorobenzo[b]thien-2-yl, 3,6-dichlorobenzo[b]thien-2-yl, 1-methylindol-3-yl, 2-methoxyquinol-3-yl, 2,6-dimethoxyquinol-3-yl, 2-ethylthioquinol-3-yl, 2-chloro-6-methoxyquinol-3-yl, 3,7-dichloroquinol-8-yl, 2-methylchroman-3-yl, 2,2-dimethylchroman-3-yl, 2-methyl-2H-chromen-3-yl, 2,2-dimethyl-2H-chromen-3-yl, 2-methylimidazo[1,2-a]pyrid-3-yl, 4,6,8-trimethylazulen-1-yl, 6,7-dimethyl-1,2,3,4-tetrahydronaphth-1-yl, 6-methoxy-1,2,3,4-tetrahydronaphth-2-yl and 2,2-dimethyl-cis-octahydrobenzo[b]fur-4-yl.

In formula I, $R^3$ is straight-chain or branched alkyl of 1 to 4 carbon atoms, eg. methyl, ethyl, n-propyl, i-propyl, n-butyl, sec.-butyl, i-butyl or tert.-butyl, and $R^4$ is propargyl, alkyl of 1 to 3 carbon atoms, alkenyl of 3 or 4 carbon atoms or haloalkenyl of 3 or 4 carbon atoms and not more than 3 halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl, 1,1,2-trichloroprop-1-en-3-yl or 1,2-dibromoprop-1-en-3-yl (cis/trans).

Examples of suitable compounds of the formula I are alkali metal salts, in particular potassium or sodium salts, alkaline earth metal salts, in particular calcium, magnesium or barium salts, manganese, copper, zinc or iron salts and tetraalkylammonium salts, eg. tetramethylammonium, tetraethylammonium or tetrabutylammonium salts, trialkylsulfonium salts, eg. trimethylsulfonium salts, and trialkylsulfoxonium salts, eg. trimethylsulfoxonium salts.

Preferred compounds of the formula I are those in which $R^1$ is a fused ring which is unsubstituted or substituted by $C_1-C_3$-alkyl, $C_1-C_3$-alkoxy, $C_1-C_3$-alkylthio or halogen and is selected from the group consisting of benzo[b]thienyl, benzo-1,3-dioxolyl, quinolyl, tetrahydronaphthyl, 4a,7,8,8a-tetrahydro-2H,5H-pyrano[4,3-b]pyranyl and 3,4,4a,7,8,8a-hexahydro-2H,5H-pyrano[4,3-]pyranyl, for example 3-benzo[b]thienyl, benzo-1,3-dioxol-5-yl, 3-quinolyl, 8-quinolyl, 1,2,3,4-tetrahydro-2-naphthyl, 4a,7,8,8a-tetrahydro-2H,5H-pyrano[4,3-b]pyran-3-yl and 3,4,4a,7,8,8a-hexahydro-2H,5H-pyrano[4,3-b[pyran-3-yl.

The compounds of the formula I can be obtained by reacting a 2-alkanoylcyclohexane-1,3-dione of the formula

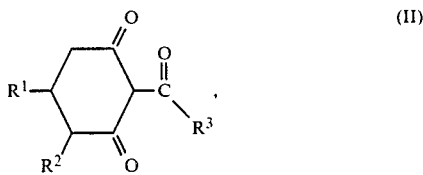
(II)

where $R^1$, $R^2$ and $R^3$ have the above meanings, with a hydroxylamine derivative $R^4O-NH_3Y$, where $R^4$ has the above meanings and Y is an anion.

The reaction is advantageously carried out in the heterogeneous phase in an inert diluent at from 0° to 80° C. or at from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly well at a pH of from 2 to 9, in particular from 4.5 to 5.5. The pH is advantageously established by adding an acetate, for example an alkali metal acetate, in particular sodium acetate or potassium acetate, or a mixture of these. Alkali metal acetates are added in an amount of, for example, from 0.5 to 2 moles per mole of the ammonium compound of the formula $R^4O-NH_3Y$.

Examples of suitable solvents are dimethylsulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, eg. methylene chloride, and distilling off the solvent under reduced pressure.

The compounds of the formula I can furthermore be obtained by reacting a compound of the formula II with a hydroxylamine of the formula $R^4O-NH_2$, where $R^4$ has the above meanings, in an inert diluent at from 0° C. to the boiling point of the reaction mixture, in particular from 15° to 70° C. If required, the hydroxylamine can be employed in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. The base used may also be a sodium alcoholate or a potassium alcoholate.

The other metal salts, eg. the manganese, copper, zinc, iron, calcium, magnesium and barium salts, can be prepared from the sodium salts by reaction with the corresponding metal chlorides in aqueous solution. The tetraalkylammonium salts of the compounds of the formula I can be obtained by treating these compounds with a tetraalkylammonium hydroxide, while the trialkylsulfonium and trialkylsulfoxonium salts can be obtained by reacting the sodium salts with trialkylsulfonium iodide and trialkylsulfoxonium iodide respectively.

The compounds of the formula II are novel. They can be prepared from cyclohexane-1,3-diones of the formula III, which may also occur in the tautomeric forms represented by formulae IIIa and IIIb

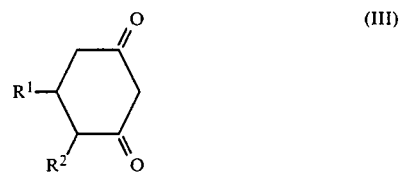
(III)

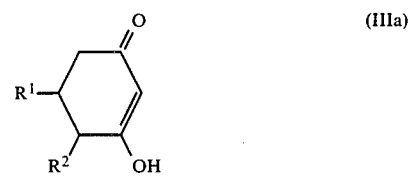
(IIIa)

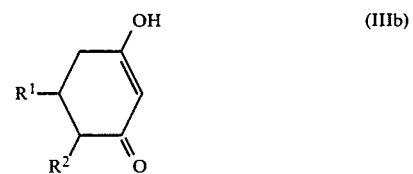
(IIIb)

using a conventional method (Tetrahedron Lett. 29 (1975), 2491).

It is also possible to prepare compounds of the formula II via the enol-ester intermediates; these are obtained, possibly as an isomer mixture, in the conversion of compounds of the formula II, and undergo rearrangement in the presence of an imidazole or pyridine derivative (Japanese Preliminary Published Application No. 79/063,052).

The compounds of the formula III are obtained by a conventional process, as shown in the equation below:

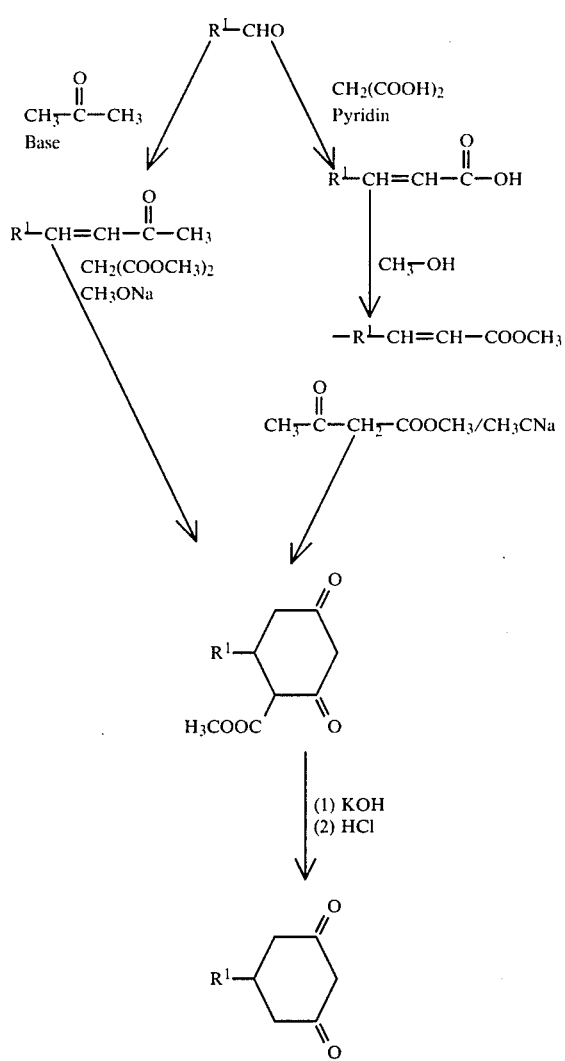

The aldehydes of the formula R¹-CHO are obtainable by a conventional process, eg. a Vilsmeier reaction, metalization and reaction with dimethylformamide, cleavage of acetals, the Sommelet reaction, hydroformylation, oxidation of primary alcohols, hydrolysis of geminal dihalides or reduction of acyl chlorides, carboxylates and acyl nitriles.

The Examples which follow illustrate the preparation of the cyclohexane-1,3-dione derivatives of the formula I. Parts by weight bear the same relation to parts by volume as that of the kilogram to the liter.

EXAMPLE 1

4.6 parts by weight of 2-butyryl-5-(benzo[b]fur-2-yl)-cyclohexane-1,3-dione, 1.2 parts by weight of allyloxyamine and 30 parts by volume of ethanol were stirred for 12 hours at room temperature. The solvent was distilled off under reduced pressure, the residue was taken up in 50 parts of dichloromethane, the solution was washed twice with water and dried over sodium sulfate, and the solvent was distilled off under reduced pressure. 2-(1-Allyloxyaminobutylidene)-5-(benzo[b]fur-2-yl)-cyclohexane-1,3-dione was obtained as a viscous oil in a yield of 92% (compound no. 2).

$C_{21}H_{23}NO_4$ (353) Calculated: C 71.4, H 6.6, N 3.9; Found: C 71.4, H 6.2, N 3.4.

EXAMPLE 2

7.0 parts by weight of 2-butyryl-5-(benzo[b]thien-2-yl)-cyclohexane-1,3-dione, 2.4 parts by weight of ethoxyammonium chloride, 2.1 parts by weight of sodium bicarbonate and 70 parts of methanol were stirred for 12 hours at room temperature. The solvent was distilled off under reduced pressure, the residue was extracted with 50 parts of water and 50 parts of methylene chloride, and the combined organic phases were washed with water, dried over sodium sulfate and evaporated down under reduced pressure.

2-(1-Ethoxyaminobutylidene)-5-(benzo[b]thien-2-yl)-cyclohexane-1,3-dione was obtained as a pale brown solid of melting point 73°–76° C. (compound no. 10), the yield being 95%.

$C_{20}H_{23}NO_3S$ (357) Calculated: C 67.2, H 6.4, N 3.9; Found: C 67.0, H 6.4, N 4.6.

The following compounds of the formula I are obtained by similar reactions:

| No. | R¹ | R² | R³ | R⁴ | $n_D$/m.p. [°C.] |
|---|---|---|---|---|---|
| 1 | 2-benzo[b]furyl | H | n-C₃H₇ | C₂H₅ | |
| 2 | 2-benzo[b]furyl | H | n-C₃H₇ | CH₂—CH=CH₂ | |
| 3 | 2-benzo[b]furyl | H | C₂H₅ | CH₂—CH=CH₂ | |
| 4 | 2-ethyl-3-benzo[b]furyl | H | C₂H₅ | C₂H₅ | 1.5621 (21° C.) |
| 5 | 2-ethyl-3-benzo[b]furyl | H | C₂H₅ | n-C₃H₇ | |
| 6 | 2-ethyl-3-benzo[b]furyl | H | C₂H₅ | CH₂—CH=CH₂ | 1.5695 (21° C.) |
| 7 | 2-ethyl-3-benzo[b]furyl | H | n-C₃H₇ | CH₂—C≡CH | |
| 8 | 2-ethyl-3-benzo[b]furyl | H | n-C₃H₇ | CH₂—CCl=CCl₂ | |
| 9 | 2-ethyl-3-benzo[b]furyl | COOCH₃ | n-C₃H₇ | C₂H₅ | |
| 10 | 2-benzo[b]thienyl | H | n-C₃H₇ | C₂H₅ | 76–79 |
| 11 | 2-benzo[b]thienyl | H | n-C₃H₇ | CH₂—CH=CH₂ | 50 |
| 12 | 2-benzo[b]thienyl | H | n-C₃H₇ | n-C₃H₇ | 54 |
| 13 | 2-benzo[b]thienyl | H | n-C₃H₇ | CH₂—C≡CH | 72 |
| 14 | 2-benzo[b]thienyl | H | n-C₃H₇ | CH₂—CH=CHCl | 82 |
| 15 | 3-benzo[b]thienyl | H | C₂H₅ | C₂H₅ | |
| 16 | 3-benzo[b]thienyl | H | C₂H₅ | CH₂—CH=CH₂ | 1.6158 (24° C.) |
| 17 | 3-benzo[b]thienyl | H | n-C₃H₇ | C₂H₅ | 1.5995 (23° C.) |
| 18 | 3-benzo[b]thienyl | H | n-C₃H₇ | CH₂—CH=CH₂ | 1.6038 (23° C.) |
| 19 | 3-chloro-2-benzo[b]thienyl | H | n-C₃H₇ | C₂H₅ | 69–70 |
| 20 | 3,6-dichloro-2-benzo[b]thienyl | H | n-C₃H₇ | C₂H₅ | 106–108 |
| 21 | 3,6-dichloro-2-benzo[b]thienyl | H | n-C₃H₇ | CH₂—CH=CH₂ | 71–74 |
| 22 | 1-methyl-3-indolyl | H | n-C₃H₇ | CH₂—CH=CH₂ | |
| 23 | 1-methyl-3-indolyl | H | n-C₃H₇ | C₂H₅ | |
| 24 | 1-methyl-3-indolyl | H | C₂H₅ | C₂H₅ | |
| 25 | 1-methyl-3-indolyl | H | C₂H₅ | CH₂—CH=CH₂ | |
| 26 | 2-benzothiazolyl | H | C₂H₅ | CH₂—CH=CH₂ | |

-continued

| No. | R¹ | R² | R³ | R⁴ | $n_D$/m.p. [°C.] |
|---|---|---|---|---|---|
| 27 | 2-benzothiazolyl | H | C₂H₅ | C₂H₅ | |
| 28 | 2-benzothiazolyl | H | n-C₃H₇ | C₂H₅ | |
| 29 | 2-benzothiazolyl | H | n-C₃H₇ | CH₂—CH=CH₂ | |
| 30 | 3-quinolyl | H | n-C₃H₇ | C₂H₅ | 112–115 |
| 31 | 3-quinolyl | H | n-C₃H₇ | CH₂—CH=CH₂ | 64 |
| 32 | 2-methoxy-3-quinolyl | H | n-C₃H₇ | C₂H₅ | 105–112 |
| 33 | 2-methoxy-3-quinolyl | H | n-C₃H₇ | CH₂—CH=CH₂ | 80–84 |
| 34 | 2-ethylthio-3-quinolyl | H | n-C₃H₇ | CH₂—CH=CH₂ | |
| 35 | 2-ethylthio-3-quinolyl | H | n-C₃H₇ | C₂H₅ | 103–105 |
| 36 | 2,6-dimethyl-3-quinolyl | H | n-C₃H₇ | C₂H₅ | 114–116 |
| 37 | 2-chloro-6-methoxy-3-quinolyl | H | n-C₃H₇ | C₂H₅ | 100–107 |
| 38 | 4-quinolyl | H | n-C₃H₇ | C₂H₅ | |
| 39 | 4-quinolyl | H | n-C₃H₇ | CH₂—CH=CH₂ | |
| 40 | 3,7-dichloro-8-quinolyl | H | n-C₃H₇ | CH₂—CH=CH₂ | |
| 41 | 3,7-dichloro-8-quinolyl | H | n-C₃H₇ | C₂H₅ | |
| 42 | 2-quinoxalinyl | H | n-C₃H₇ | C₂H₅ | |
| 43 | 2-quinoxalinyl | H | n-C₃H₇ | CH₂—CH=CH₂ | |
| 44 | 2-quinoxalinyl | H | C₂H₅ | CH₂—CH=CH₂ | |
| 45 | 2-quinoxalinyl | H | C₂H₅ | C₂H₅ | |
| 46 | 3-chromanyl | H | n-C₃H₇ | C₂H₅ | 88–92 |
| 47 | 3-chromanyl | H | n-C₃H₇ | CH₂—CH=CH₂ | 67–71 |
| 48 | 3-chromanyl | H | C₂H₅ | CH₂—CH=CH₂ | |
| 49 | 3-chromanyl | H | C₂H₅ | C₂H₅ | |
| 50 | 2-methyl-3-chromanyl | H | C₂H₅ | C₂H₅ | |
| 51 | 2-methyl-3-chromanyl | H | C₂H₅ | CH₂—CH=CH₂ | |
| 52 | 2-methyl-3-chromanyl | H | n-C₃H₇ | CH₂—CH=CH₂ | |
| 53 | 2-methyl-3-chromanyl | H | n-C₃H₇ | C₂H₅ | |
| 54 | 2,2-dimethyl-3-chromanyl | H | n-C₃H₇ | C₂H₅ | |
| 55 | 2,2-dimethyl-3-chromanyl | H | n-C₃H₇ | CH₂—CH=CH₂ | |
| 56 | 2,2-dimethyl-3-chromanyl | H | C₂H₅ | CH₂—CH=CH₂ | |
| 57 | 2,2-dimethyl-3-chromanyl | H | C₂H₅ | C₂H₅ | |
| 58 | 2-methyl-2H—chromen-3-yl | H | C₂H₅ | C₂H₅ | 1.5838 (27° C.) |
| 59 | 2-methyl-2H—chromen-3-yl | H | C₂H₅ | CH₂—CH=CH₂ | 1.5880 (27° C.) |
| 60 | 2-methyl-2H—chromen-3-yl | H | n-C₃H₇ | CH₂—CH=CH₂ | 1.5830 (22° C.) |
| 61 | 2-methyl-2H—chromen-3-yl | H | n-C₃H₇ | C₂H₅ | 1.5786 (23° C.) |
| 62 | 2,2-dimethyl-2H—chromen-3-yl | H | n-C₃H₇ | C₂H₅ | 1.5744 (26° C.) |
| 63 | 2,2-dimethyl-2H—chromen-3-yl | H | n-C₃H₇ | CH₂—CH=CH₂ | 1.5798 (23° C.) |
| 64 | 2,2-dimethyl-2H—chromen-3-yl | H | C₂H₅ | CH₂—CH=CH₂ | 1.5804 (26° C.) |
| 65 | 2,2-dimethyl-2H—chromen-3-yl | H | C₂H₅ | C₂H₅ | 1.5783 (26° C.) |
| 66 | benzo-1,3-dioxol-5-yl | H | C₂H₅ | C₂H₅ | 1.5638 (23° C.) |
| 67 | benzo-1,3-dioxol-5-yl | H | C₂H₅ | CH₂—CH=CH₂ | 1.5755 (23° C.) |
| 68 | benzo-1,3-dioxol-5-yl | H | n-C₃H₇ | CH₂—CH=CH₂ | 67–68 |
| 69 | benzo-1,3-dioxol-5-yl | H | n-C₃H₇ | C₂H₅ | 51–53 |
| 70 | 2,3-dihydro-5-benzo[b]furyl | H | n-C₃H₇ | C₂H₅ | |
| 71 | 2,3-dihydro-5-benzo[b]furyl | H | n-C₃H₇ | CH₂—CH=CH₂ | |
| 72 | 2,3-dihydro-5-benzo[b]furyl | H | C₂H₅ | CH₂—CH=CH₂ | |
| 73 | 2,3-dihydro-5-benzo[b]furyl | H | C₂H₅ | C₂H₅ | |
| 74 | 1-naphthyl | H | n-C₃H₇ | CH₂—CH=CH₂ | 52–56 |
| 75 | 1-naphthyl | H | n-C₃H₇ | C₂H₅ | 86–88 |
| 76 | 1-naphthyl | COOCH₃ | n-C₃H₇ | C₂H₅ | 105–110 |
| 77 | 1-naphthyl | CN | n-C₃H₇ | C₂H₅ | |
| 78 | 1-naphthyl | CN | n-C₃H₇ | CH₂—CH=CH₂ | |
| 79 | 1-naphthyl | CN | C₂H₅ | CH₂—CH=CH₂ | |
| 80 | 1-naphthyl | CN | C₂H₅ | C₂H₅ | |
| 81 | 1-naphthyl | CH₃ | n-C₃H₇ | C₂H₅ | |
| 82 | 1-naphthyl | CH₃ | n-C₃H₇ | CH₂—CH=CH₂ | |
| 83 | 1-naphthyl | CH₃ | n-C₃H₇ | n-C₃H₇ | |
| 84 | 1-naphthyl | CH₃ | n-C₃H₇ | CH₂—C≡CH | |
| 85 | 1-naphthyl | CH₃ | n-C₃H₇ | CH₂—CH=CHCl | |
| 86 | 1-naphthyl | CH₃ | n-C₃H₇ | CH₂—CCl=CCl₂ | |
| 87 | 2-naphthyl | H | n-C₃H₇ | CH₂—CH=CH₂ | |
| 88 | 2-naphthyl | H | n-C₃H₇ | C₂H₅ | |
| 89 | 2-naphthyl | H | C₂H₅ | CH₂—CH=CH₂ | 1.6015 (23° C.) |
| 90 | 2-naphthyl | H | C₂H₅ | C₂H₅ | |
| 91 | 2-naphthyl | COOCH₃ | n-C₃H₇ | C₂H₅ | 105 |
| 92 | 2-naphthyl | COOCH₃ | n-C₃H₇ | CH₂—CH=CH₂ | |
| 93 | 2-naphthyl | COOCH₃ | C₂H₅ | C₂H₅ | 52 |
| 94 | 2-naphthyl | COOCH₃ | C₂H₅ | CH₂—CH=CH₂ | 50–55 |
| 95 | 1-azulenyl | H | n-C₃H₇ | C₂H₅ | |
| 96 | 1-azulenyl | H | n-C₃H₇ | CH₂—CH=CH₂ | |
| 97 | 1-azulenyl | H | C₂H₅ | CH₂—CH=CH₂ | |
| 98 | 1-azulenyl | H | C₂H₅ | C₂H₅ | |
| 99 | 4,6,8-trimethyl-1-azulenyl | H | C₂H₅ | C₂H₅ | |
| 100 | 4,6,8-trimethyl-1-azulenyl | H | C₂H₅ | CH₂—CH=CH₂ | |
| 101 | 4,6,8-trimethyl-1-azulenyl | H | n-C₃H₇ | CH₂—CH=CH₂ | |
| 102 | 4,6,8-trimethyl-1-azulenyl | H | n-C₃H₇ | C₂H₅ | |
| 103 | 6,7-dimethyl-1,2,3,4-tetrahydro-1-naphthyl | H | n-C₃H₇ | C₂H₅ | |
| 104 | 6,7-dimethyl-1,2,3,4-tetrahydro-1-naphthyl | H | n-C₃H₇ | CH₂—CH=CH₂ | |
| 105 | 1,2,3,4-tetrahydro-2-naphthyl | H | n-C₃H₇ | C₂H₅ | |

-continued

| No. | R¹ | R² | R³ | R⁴ | nD/m.p. [°C.] |
|---|---|---|---|---|---|
| 106 | 1,2,3,4-tetrahydro-2-naphthyl | H | n-C₃H₇ | CH₂—CH=CH₂ | |
| 107 | 1,2,3,4-tetrahydro-2-naphthyl | H | C₂H₅ | CH₂—CH=CH₂ | |
| 108 | 1,2,3,4-tetrahydro-2-naphthyl | H | C₂H₅ | C₂H₅ | |
| 109 | 6-methoxy-1,2,3,4-tetrahydro-2-naphthyl | H | C₂H₅ | C₂H₅ | |
| 110 | 6-methoxy-1,2,3,4-tetrahydro-2-naphthyl | H | C₂H₅ | CH₂CH=CH₂ | 104–106 |
| 111 | 6-methoxy-1,2,3,4-tetrahydro-2-naphthyl | H | n-C₃H₇ | CH₂CH=CH₂ | 56–58 |
| 112 | 6-methoxy-1,2,3,4-tetrahydro-2-naphthyl | H | n-C₃H₇ | C₂H₅ | |
| 113 | 1-inandyl | H | n-C₃H₇ | C₂H₅ | |
| 114 | 1-inandyl | H | n-C₃H₇ | CH₂—CH=CH₂ | |
| 115 | 2,2-dimethyl-cis-octahydro-4-benzo[b]furyl | H | n-C₃H₇ | CH₂—CH=CH₂ | |
| 116 | 2,2-dimethyl-cis-octahydro-4-benzo[b]furyl | H | n-C₃H₇ | C₂H₅ | |
| 117 | cis-hexahydro-benzo-1,3-dioxyl-5-yl | H | n-C₃H₇ | C₂H₅ | |
| 118 | cis-hexahydro-benzo-1,3-dioxyl-5-yl | H | n-C₃H₇ | CH₂—CH=CH₂ | |
| 119 | cis-hexahydro-benzo-1,3-dioxyl-5-yl | H | n-C₃H₇ | n-C₃H₇ | |
| 120 | cis-hexahydro-benzo-1,3-dioxol-5-yl | H | n-C₃H₇ | CH₂—C≡CH | |
| 121 | cis-hexahydro-benzo-1,3-dioxol-5-yl | H | n-C₃H₇ | CH₂—CH=CHCl | |
| 122 | cis-hexahydro-benzo-1,3-dioxol-5-yl | H | n-C₃H₇ | CH₂—CCl=CCl₂ | |
| 123 | 4a,7,8,8a-tetrahydro-2H,5H—pyrano[4,3-b]pyran-3-yl | H | n-C₃H₇ | C₂H₅ | 1.5368 (30° C.) |
| 124 | 4a,7,8,8a-tetrahydro-2H,5H—pyrano[4,3-b]pyran-3-yl | H | n-C₃H₇ | CH₂—CH=CH₂ | 1.5430 (30° C.) |
| 125 | 2-benzo[b]furyl | H | C₂H₅ | C₂H₅ | |
| 126 | 2-benzo[b]furyl | H | C₂H₅ | CH₂—CH=CH₂ | |
| 127 | 3-methyl-2-benzo[b]furyl | H | C₂H₅ | CH₂—CH=CH₂ | |
| 128 | 3-methyl-2-benzo[b]furyl | H | C₂H₅ | C₂H₅ | |
| 129 | 3-methyl-2-benzo[b]furyl | H | n-C₃H₇ | C₂H₅ | |
| 130 | 3-methyl-2-benzo[b]furyl | H | n-C₃H₇ | CH₂—CH=CH₂ | |
| 131 | 2-benzo[b]thienyl | H | C₂H₅ | CH₂—CH=CH₂ | |
| 132 | 2-benzo[b]thienyl | H | C₂H₅ | C₂H₅ | |
| 133 | 3-chloro-2-benzo[b]thienyl | H | C₂H₅ | C₂H₅ | |
| 134 | 3-chloro-2-benzo[b]thienyl | H | C₂H₅ | CH₂—CH=CH₂ | |
| 135 | 3,6-dichloro-2-benzo[b]thienyl | H | C₂H₅ | C₂H₅ | |
| 136 | 3,6-dichloro-2-benzo[b]thienyl | H | C₂H₅ | CH₂—CH=CH₂ | |
| 137 | 3-quinolyl | H | C₂H₅ | CH₂—CH=CH₂ | |
| 138 | 3-quinolyl | H | C₂H₅ | C₂H₅ | |
| 139 | 2-methoxy-3-quinolyl | H | C₂H₅ | C₂H₅ | |
| 140 | 2-methoxy-3-quinolyl | H | C₂H₅ | CH₂—CH=CH₂ | |
| 141 | 2-ethylthio-3-quinolyl | H | C₂H₅ | CH₂—CH=CH₂ | |
| 142 | 2-ethylthio-3-quinolyl | H | C₂H₅ | C₂H₅ | |
| 143 | 2,6-dimethoxy-3-quinolyl | H | C₂H₅ | C₂H₅ | |
| 144 | 2,6-dimethoxy-3-quinolyl | H | C₂H₅ | CH₂—CH=CH₂ | |
| 145 | 2-chloro-6-methoxy-3-quinolyl | H | C₂H₅ | CH₂—CH=CH₂ | |
| 146 | 2-chloro-6-methoxy-3-quinolyl | H | C₂H₅ | C₂H₅ | |
| 147 | 4-quinolyl | H | C₂H₅ | C₂H₅ | |
| 148 | 4-quinolyl | H | C₂H₅ | CH₂—CH=CH₂ | |
| 149 | 3,7-dichloro-8-quinolyl | H | C₂H₅ | C₂H₅ | |
| 150 | 3,7-dicholro-8-quinolyl | H | C₂H₅ | CH₂—CH=CH₂ | |
| 151 | 1-naphthyl | H | C₂H₅ | CH₂—CH=CH₂ | |
| 152 | 1-naphthyl | H | C₂H₅ | C₂H₅ | |
| 153 | 6,7-dimethyl-1,2,3,4-tetrahydro-1-naphthyl | H | C₂H₅ | C₂H₅ | |
| 154 | 6,7-dimethyl-1,2,3,4-tetrahydro-1-naphthyl | H | C₂H₅ | CH₂—CH=CH₂ | |
| 155 | 1-indanyl | H | C₂H₅ | CH₂—CH=CH₂ | |
| 156 | 1-indanyl | H | C₂H₅ | C₂H₅ | |
| 157 | 2,2-dimethyl-cis-octahydro-4-benzo[b]furyl | H | C₂H₅ | C₂H₅ | |
| 158 | 2,2-dimethyl-cis-octahydro-4-benzo[b]furyl | H | C₂H₅ | CH₂—CH=CH₂ | |
| 159 | cis-hexahydro-benzo-1,3-dioxol-5-yl | H | C₂H₅ | CH₂—CH=CH₂ | |
| 160 | cis-hexahydro-benzo-1,3-dioxol-5-yl | H | C₂H₅ | C₂H₅ | |
| 161 | 4a,7,8,8a-tetrahydro-2H,5H—pyrano[4,3-b]pyran-3-yl | H | C₂H₅ | C₂H₅ | |
| 162 | 4a,7,8,8a-tetrahydro-2H,5H—pyrano[4,3-b]pyran-3-yl | H | C₂H₅ | CH₂—CH=CH₂ | |
| 163 | 1-isoquinolyl | H | n-C₃H₇ | C₂H₅ | |
| 164 | 1-isoquinolyl | H | n-C₃H₇ | CH₂—CH=CH₂ | |

-continued

| No. | R¹ | R² | R³ | R⁴ | $n_D$/m.p. [°C.] |
|---|---|---|---|---|---|
| 165 | 1-isoquinolyl | H | C₂H₅ | CH₂—CH=CH₂ | |
| 166 | 1-isoquinolyl | H | C₂H₅ | C₂H₅ | |
| 167 | 4-isoquinolyl | H | C₂H₅ | C₂H₅ | |
| 168 | 4-isoquinolyl | H | C₂H₅ | CH₂—CH=CH₂ | |
| 169 | 4-isoquinolyl | H | n-C₃H₇ | CH₂—CH=CH₂ | |
| 170 | 4-isoquinolyl | H | n-C₃H₇ | C₂H₅ | |
| 171 | 5-isoquinolyl | H | n-C₃H₇ | C₂H₅ | |
| 172 | 5-isoquinolyl | H | n-C₃H₇ | CH₂—CH=CH₂ | |
| 173 | 5-isoquinolyl | H | C₂H₅ | CH₂—CH=CH₂ | |
| 174 | 5-isoquinolyl | H | C₂H₅ | C₂H₅ | |
| 175 | 3,4,4a,7,8,8a-hexahydro-2H,5H—pyrano[4,3b]pyran-3-yl | H | n-C₃H₇ | C₂H₅ | 57–60 |
| 176 | 3,4,4a,7,8,8a-hexahydro-2H,5H—pyrano[4,3b]pyran-3-yl | H | n-C₃H₇ | CH₂—CH=CH₂ | 1.5360 (23° C.) |
| 177 | hexahydrochroman-3-yl | H | n-C₃H₇ | C₂H₅ | |
| 178 | hexahydrochroman-3-yl | H | n-C₃H₇ | CH₂—CH=CH₂ | |
| 179 | 2H—chroman-3-yl | H | n-C₃H₇ | C₂H₅ | 50–56 |
| 180 | 2H—chroman-3-yl | H | n-C₃H₇ | CH₂—CH=CH₂ | 1.5891 (32° C.) |
| 181 | 2-methyl-2H—chroman-3-yl | COOCH₃ | n-C₃H₇ | C₂H₅ | 1.5594 (26° C.) |
| 182 | 2-methyl-2H—chroman-3-yl | COOCH₃ | n-C₃H₇ | CH₂—CH=CH₂ | 1.5623 (26° C.) |
| 183 | benzo-1,3-dioxol-5-yl | H | n-C₃H₇ | CH₂—CBr=CHBr | 71 |
| 184 | benzo-1,3-dioxol-5-yl | H | C₂H₅ | CH₃ | |
| 185 | benzo-1,3-dioxol-5-yl | H | C₂H₅ | n-C₃H₇ | 1.5667 (24° C.) |
| 186 | benzo-1,3-dioxol-5-yl | H | C₂H₅ | CH₂—CH=CHCl | 1.5820 (24° C.) |
| 187 | benzo-1,3-dioxol-5-yl | H | C₂H₅ | CH₂—CCl=CCl₂ | 88–90 |
| 188 | benzo-1,3-dioxol-5-yl | H | C₂H₅ | CH₂—C≡CH | 1.5872 (23° C.) |
| 189 | 3-benzo[b]thienyl | H | n-C₃H₇ | n-C₃H₇ | 1.5935 (23° C.) |
| 190 | benzo-1,4-dioxen-6-yl | H | n-C₃H₇ | C₂H₅ | |
| 191 | benzo-1,4-dioxen-6-yl | H | n-C₃H₇ | CH₂—CH=CH₂ | |
| 192 | benzo-1,4-dioxen-6-yl | H | C₂H₅ | n-C₃H₇ | |
| 193 | benzo-1,4-dioxen-6-yl | H | C₂H₅ | CH₂—CH=CH₂ | |
| 194 | benzo-1,3-dioxol-5-yl | H | n-C₃H₇ | n-C₃H₇ | 1.5638 (24° C.) |
| 195 | 3-benzo[b]thienyl | H | n-C₃H₇ | n-C₃H₇ | 1.5935 (23° C.) |
| 196 | hexahydrochroman-3-yl | H | C₂H₅ | C₂H₅ | |
| 197 | hexahydrochroman-3-yl | H | C₂H₅ | CH₂—CH=CH₂ | |
| 198 | 4a,7,8,8a-tetrahydro-2H,5H—thiino[3,2-c]pyran-3-yl | H | n-C₃H₇ | C₂H₅ | |
| 199 | 4a,7,8,8a-tetrahydro-2H,5H—thiino[3,2-c]pyran-3-yl | H | n-C₃H₇ | CH₂—CH=CH₂ | |
| 200 | 4a,7,8,8a-tetrahydro-2H,5H—thiino[3,2-c]pyran-3-yl | H | C₂H₅ | C₂H₅ | |
| 201 | 4a,7,8,8a-tetrahydro-2H,5H—thiino[3,2-c]pyran-3-yl | H | C₂H₅ | CH₂—CH=CH₂ | |
| 202 | 3,4,4a,7,8,8a-hexahydro-2H,5H—thiino[3,2-c]pyran-3-yl | H | n-C₃H₇ | C₂H₅ | |
| 203 | 3,4,4a,7,8,8a-hexahydro-2H,5H—thiino[3,2-c]pyran-3-yl | H | n-C₃H₇ | CH₂—CH=CH₂ | |
| 204 | 3,4,4a,7,8,8a-hexahydro-2H,5H—thiino[3,2-c]pyran-3-yl | H | C₂H₅ | C₂H₅ | |
| 205 | 3,4,4a,7,8,8a-hexahydro-2H,5H—thiino[3,2-c]pyran-3-yl | H | C₂H₅ | CH₂—CH=CH₂ | |
| 206 | 4a,7,8,8a-tetrahydro-2H,5H—thiino[4,3-b]pyran-3-yl | H | n-C₃H₇ | C₂H₅ | |
| 207 | 4a,7,8,8a-tetrahydro-2H,5H—thiino[4,3-b]pyran-3-yl | H | n-C₃H₇ | CH₂—CH=CH₂ | |
| 208 | 4a,7,8,8a-terahydro-2H,5H—thiino[4,3-b]pyran-3-yl | H | C₂H₅ | C₂H₅ | |
| 209 | 4a,7,8,8a-tetrahydro-2H,5H—thiino[4,3-b]pyran-3-yl | H | C₂H₅ | CH₂—CH=CH₂ | |
| 210 | 3,4,4a,7,8,8a-hexahydro-2H,5H—thiino[4,3-b]pyran-3-yl | H | n-C₃H₇ | C₂H₅ | |
| 211 | 3,4,4a,7,8,8a-hexahydro-2H,5H—thiino[4,3-b]pyran-3-yl | H | n-C₃H₇ | CH₂—CH=CH₂ | |
| 212 | 3,4,4a,7,8,8a-hexahydro-2H,5H—thiino[4,3-b]pyran-3-yl | H | C₂H₅ | C₂H₅ | |
| 213 | 3,4,4a,7,8,8a-hexahydro-2H,5H—thiino[4,3-b]pyran-3-yl | H | C₂H₅ | CH₂—CH=CH₂ | |
| 214 | benzo-1,3-dioxol-5-yl (sodium salt) | H | C₂H₅ | C₂H₅ | >200 |
| 215 | benzo-1,3-dioxol-5-yl (tetrabutylammonium salt) | H | n-C₃H₇ | C₂H₅ | >200 |
| 216 | benzo-1,3-dioxol-5-yl (barium salt) | H | n-C₃H₇ | C₂H₅ | >200 |
| 217 | 4a,7,8,8a-tetrahydro-2H,5H—pyrano[4,3-b]pyran-3-yl | H | C₂H₅ | cis-CH₂CH=CHCl | |
| 218 | 4a,7,8,8a-tetrahydro-2H,5H—pyrano[4,3-b]pyran-3-yl | H | C₂H₅ | trans-CH₂CH=CHCl | |
| 219 | 4a,7,8,8a-tetrahydro-2H,5H—pyrano[4,3-b]pyran-3-yl | H | C₃H₇ | cis-CH₂CH=CHCl | 1.5543 (22° C.) |
| 220 | 4a,7,8,8a-tetrahydro-2H,5H—pyrano[4,3-b]pyran-3-yl | H | C₃H₇ | trans-CH₂CH=CHCl | 1.5542 (22° C.) |

| No. | R¹ | R² | R³ | R⁴ | $n_D$/m.p. [°C.] |
|-----|-----|-----|-----|-----|-----|
| 221 | 3,4,4a,7,8,8a-hexahydro-2H,5H—pyrano[4,3-b]pyran-3-yl | H | $C_2H_5$ | cis-$CH_2CH{=}CHCl$ | |
| 222 | 3,4,4a,7,8,8a-hexahydro-2H,5H—pyrano[4,3-b]pyran-3-yl | H | $C_2H_5$ | trans-$CH_2CH{=}CHCl$ | |
| 223 | 3,4,4a,7,8,8a-hexahydro-2H,5H—pyrano[4,3-b]pyran-3-yl | H | $C_3H_7$ | cis-$CH_2CH{=}CHCl$ | |
| 224 | 3,4,4a,7,8,8a-hexahydro-2H,5H—pyrano[4,3-b]pyran-3-yl | H | $C_3H_7$ | trans-$CH_2CH{=}CHCl$ | |

¹H—NMR spectroscopic data: chemical shift in δ values (ppm) in $CDCl_3$, based on tetramethylsilane as internal standard.

| Compound no. | —NH— | —O—$CH_2$— | | |
|---|---|---|---|---|
| 1 | 4.03 (q) | 6.34 (s) | | |
| 2 | 4.45 (d) | 6.34 (s) | | |
| 3 | 4.54 (d) | 6.45 (s) | " | |
| 15 | 4.15 (d) | 7.15 (s) | | |
| 34 | 4.53 (d) | 3.70 (m) | | |
| 38 | 4.10 (q) | 4.15 (m) | " | |
| 39 | 4.55 (d) | 4.20 (m) | " | |
| 40 | 4.50 (d) | 7.50 (s) | | |
| 41 | 4.10 (q) | 7.50 (s) | | |
| 70 | 4.02 (q) | 4.45 (t) | | |
| 71 | 4.53 (d) | 4.45 (t) | | |
| 87 | 4.53 (d) | 3.50 (m) | | |
| 88 | 4.12 (q) | 3.50 (m) | " | |
| 90 | 4.60 (d) | 3.50 (m) | " | |
| 92 | 4.53 (d) | 3.55 (s) | $COOCH_3$ | |
| 184 | 3.93 (s) $OCH_3$ | 5.97 (s) | —$OCH_2O$— | |

Abbreviations for signal structures:
s = singlet
q = quartet
d = doublet
m = multiplet The cyclohexane-1,3-dione derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsions. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acid with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell metal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 10 parts by weight of compound no. 10 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 3 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 38 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 74 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 40 is intimately mixed with 95 parts by weight of particulate kaolin. A dust is obtained containing 5% by weight of the active ingredient.

VIII. 30 parts by weight of compound no. 123 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 68 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. Preferably, the novel active ingredients are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and their growth stage, and varies from 0.05 to 5 kg/ha and more, but is preferably from 0.1 to 1.0 kg/ha.

The influence of cyclohexane-1,3-dione derivatives of the formula I on the growth of unwanted and crop plants is demonstrated in greenhouse experiments.

The vessels employed were plastic flowerposts having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean and rice plants used for postemergence treatment were grown in a peat-enriched substrate. No impairment of the results is to be feared because the compounds were applied to the foliage. For this treatment, either plants which had been sown directly in the pots and grown there were selected, or plants which had been grown from seedlings and were transplanted to the pots a few days before treatment. No covers were placed on the pots in this treatment method. The application rates for postemergence treatment varied from ingredient to ingredient, and were 0.125, 0.25, 0.5 or 3.0 kg of active ingredient per hectare.

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, denoting no damage or normal emergence, and 100 denoting nonemergence or complete destruction of at least the visible plant parts.

The plants employed in the experiments were *Alopecurus myosuroides, Avena fatua, Avena sativa, Beta vulgaris, Bromus inermis, Echinochloa crus-galli, Glycine max., Gossypium hirsutum, Hordeum vulgare, Lolium multiflorum, Oryza sativa,* Panicum spp., *Poa pratensis, Setaria italica, Sorghum halepense, Triticum aestivum,* and *Zea mays.*

Preemergence treatment

On preemergence application, for example active ingredients nos. 3, 30, 37, 38, 39, 40, 74, 89, 123 and 124, applied at a rate of 3.0 kg/ha, had a very good herbicidal action on grass species. Active ingredients nos. 12, 13 and 14, for instance, also combated *Lolium multiflorum* without damaging the oat crop plants.

Postemergence treatment

On postemergence application, for example active ingredients nos. 123, 124 and 175, applied at a rate of 0.125 kg/ha, had a very good action on unwanted grassy plants without damaging broadleaved crop plants. Active ingredients nos. 68, 69 and 70, at 0.25 kg/ha, also combated unwanted grassy plants without damaging broadleaved crop plants. Compound no. 113, at the same application rate, selectively combated unwanted grasses in cereals, and compounds nos. 41 and 30, at 0.5 kg/ha, combated unwanted grasses in wheat. Compound no. 67, at 0.125 kg/ha, had a considerable herbicidal action on *Echinochloa crus-galli*, a weed important in rice, while causing only slight damage to the crop plants. At a rate of 3.0 kg/ha, compounds nos. 33, 36, 63, 65, 110, 111, 215 and 216 were highly effective on grass species.

In view of the good tolerance of the compounds according to the invention by numerous crop plants, and the numerous application methods possible, they may be used in a large number of crops for eliminating the growth of unwanted grasses or grassy crop plants growing where they are not desired.

The compounds may be employed for instance in the following crops:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora Coffea liberica) | coffee plants |
| Cucumis melo | melons |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plant |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I may be mixed and applied together with numerous other herbicidal active ingredients. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives having a structure different from that of formula I, and other herbicidal active ingredients.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. A cyclohexane-1,3-dione derivative of the formula

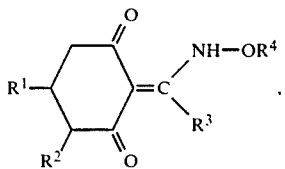
(I)

whre $R^1$ is 4a,7,8,8a-tetrahydro-2H,5H-pyrano[4,3-b]pyranyl or 3,4,4a,7,8,8a-hexahydro-2H,5H-pyrano[4,3-b]pyranyl $R^2$ is hydrogen, methoxycarbonyl, ethoxycarbonyl, methyl or cyano, $R^3$ is $C_1$–$C_4$-alkyl and $R^4$ is $C_1$–$C_3$-alkyl, $C_3$–$C_4$-alkenyl, $C_3$–$C_4$-haloalkenyl containing 1 to 3 halogen substituents, or propargyl, or a salt thereof.

2. A cyclohexane-1,3-dione derivative of the formula I as defined in claim 1, where $R^2$ is hydrogen.

3. A cyclohexane-1,3-dione derivative of the formula I as defined in claim 1, where $R^1$ is 3,4,4a,7,8,8a-hexahydro-2H,5H-pyrano[4,3-b]pyran-3-yl, $R^2$ is hydrogen, $R^3$ is n-propyl and $R^4$ is ethyl.

4. A cyclohexane-1,3-dione derivative of the formula I as defined in claim 1, where $R^1$ is 4a,7,8,8a-tetrahydro-2H,5H-pyrano[4,3-b]pyran-3-yl, $R^2$ is hydrogen, $R^3$ is n-propyl and $R^4$ is ethyl.

5. A herbicide containing inert additives and a herbicidally effective amount of a cyclohexane-1,3-dione derivative of the formula I as defined in claim 1.

6. A process for combating the growth of unwanted plants, wherein the unwanted plants and/or the area to be kept free from unwanted plant growth are treated with a herbicidally effective amount of a cyclohexane-1,3-dione derivative of the formula I as defined in claim 1.

* * * * *